United States Patent [19]

Blanquaert

[11] 4,261,063

[45] Apr. 14, 1981

[54] TITANIUM OR TITANIUM ALLOY PIN TO BE FIXED IN LONG BONES

[75] Inventor: Daniel Blanquaert, Paris, France

[73] Assignee: Ceraver, Paris, France

[21] Appl. No.: 51,571

[22] Filed: Jun. 25, 1979

[30] Foreign Application Priority Data

Jun. 29, 1978 [FR] France ................ 78 19448

[51] Int. Cl.³ ............................................. A61F 1/24
[52] U.S. Cl. ........................................ 3/1.91; 3/1.91; 128/92 C; 128/92 CA
[58] Field of Search ............... 128/92, 92 C, 92 CA, 128/92 BC; 3/1.91, 1.911

[56] References Cited

U.S. PATENT DOCUMENTS

| | | | |
|---|---|---|---|
| 3,643,658 | 2/1972 | Steinemenan | 3/1.9 X |
| 3,886,600 | 6/1975 | Kahn et al. | 3/1.91 |
| 3,996,625 | 12/1976 | Noiles | 128/92 C |
| 4,064,567 | 12/1977 | Burstein et al. | 128/92 CA X |

OTHER PUBLICATIONS

Vitalium Surgical Appliances, (Catalog) by Austenal Co., New York, N. Y. 1964, p. 65, Vitallium Wire Mesh (#6510).

*Primary Examiner*—Stephen C. Pellegrino
*Attorney, Agent, or Firm*—Sughrue, Rothwell, Mion, Zinn and Macpeak

[57] ABSTRACT

A titanium or titanium alloy pin for cement-free fixing in a long bone for a joint prosthesis or for bone repair, said pin being surrounded by a lattice of titanium wire with a mesh size of at least 0.3 mm. The pin has a rectangular cross-section and two of its surfaces have respective longitudinal grooves (3) which are notched transversely to form shoulders (5) perpendicular to the pin axis, said shoulders giving the pin a scaly profile. Application to a total prosthesis of the hip.

10 Claims, 3 Drawing Figures

TITANIUM OR TITANIUM ALLOY PIN TO BE FIXED IN LONG BONES

FIELD OF THE INVENTION

The present invention relates to a titanium or titanium alloy pin for cement-free fixing in long bones for a joint prosthesis and for bone repair, said pin being surrounded by a lattice of titanium wire with a mesh size of at least 0.3 mm.

BACKGROUND OF THE INVENTION

The applicants' German patent No. 2628284 (no English language equivalent) has already described a titanium or titanium alloy pin of this type which has two longitudinal grooves and is surrounded by a metal lattice with a mesh size of at least 0.3 welded to the pin, the grooves preferably containing a substance which facilitates the regrowth of bone tissue.

However, such a pin does not completely reinforce the surface of the prosthesis with bone tissue formed by regrowth of such tissue and does not provide very great mechanical strength of the pin in long bones.

SUMMARY OF THE INVENTION

Preferred embodiments of the present invention provide a titanium or titanium alloy pin in which an improved composite structure of the metal lattice and bone tissue is obtained, said composite structure having a modulus of elasticity close to that of the cortical bone tissue. Also such pins can be simple to manufacture and tend to promote substantially even growth of bone tissue along their entire length with little danger of subsequent necrosis, the finally installed pins being resistant to loosening.

The present invention provides a pin for cement-free fixing in a long bone to form a prosthesis of a joint or for bone repair, said pin being surrounded by a lattice of titanium wire with a mesh size of at least 0.3 mm, having a substantially rectangular cross-section and wherein at least two of its opposite surfaces each includes a longitudinal groove which is notched transversely to form shoulders disposed in planes perpendicular to the general axis of the pin.

Preferably, the shoulders are evenly spaced out and they are at a constant distance from the plane of symmetry of the pin between the opposite surfaces, so that the two opposite surfaces have a scaly profile.

Also, in a preferred embodiment, the pin is surrounded by two or three superposed lattices.

The pin itself and the lattice or lattices are advantageously coated with a coating which protects it against long-term oxidation of the titanium.

A titanium or titanium alloy femoral pin for a hip prosthesis and embodying the invention is described hereinbelow by way of an example and with reference to the accompanying drawing.

DESCRIPTION OF THE PREFERRED EMBODIMENT

Figure 1:
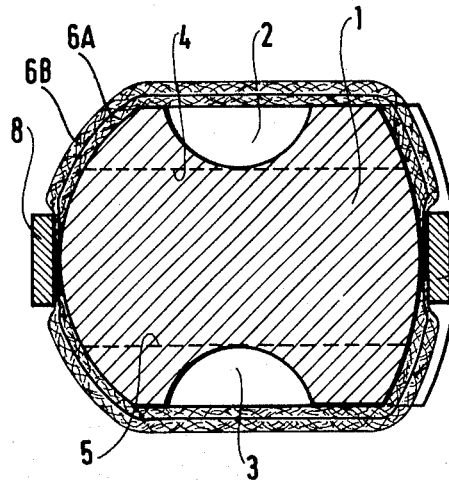
FIG. 1 is a cross-section of the pin, perpendicular to its axis, along a line I—I of FIG. 2.

The pin illustrated in cross-section in FIG. 1 has a solid portion 1 in either side of which there are cut two cylindrical grooves 2 and 3 each of which has a semicircular cross-section. At regular axially-separated intervals, the pin has shoulders 4 and 5 cut therein, along planes perpendicular to the pin axis. These shoulders form successive notches which can be seen better in FIG. 3. The shoulders allow the pin to be fixed securely in the medular duct of the femur by the re-growth of bone tissue in contact therewith. The pin is surrounded by two superposed lattices 6 of titanium or titanium alloy wire whose various layers are welded to the pin body by electron bombardment of longitudinal strips 7 and 8 disposed on the outside of the lattices.

Figure 2:
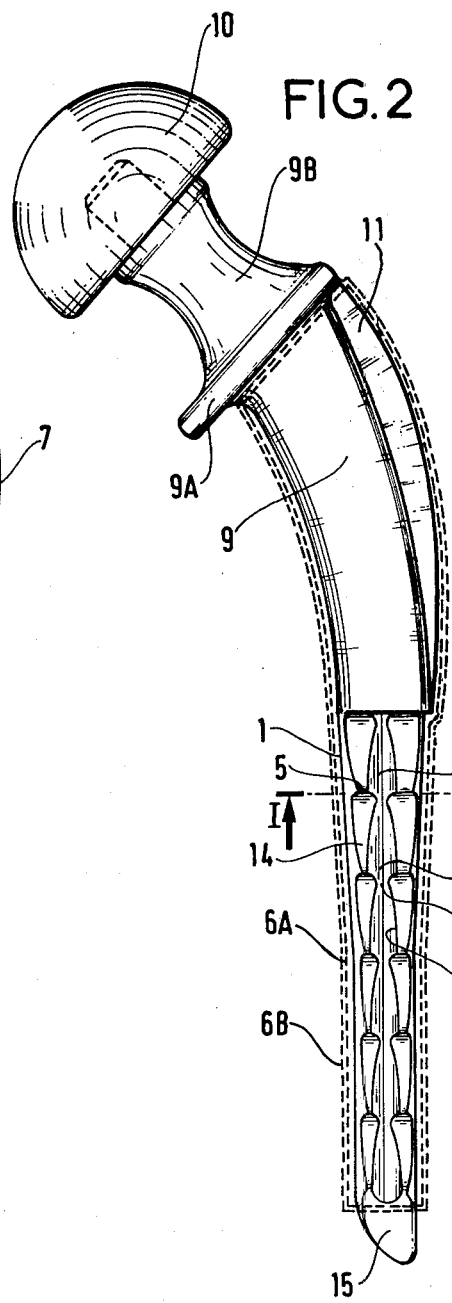
FIG. 2 is a side elevation of the pin.

FIG. 2 is a general side elevation of the pin without the metal lattice which surrounds it (and which is disposed in the position shown by dashed lines). The figure shows the longitudinal grooves 3 and the notches such as 5 for fixing the pin securely in the femur. The actual pin is connected to the spherical head 10 by a curved portion 9, followed by a support rim 9A resting on the upper end of the femur after removal of its original head, and finally a neck 9B. The angle formed by the axis of the pin 1 and of the spherical head 10 is about 132°. A solid strengthening piece 11 on the great trochanter side is designed to prevent any rotation of the pin in the bone. The metal lattice 6 is fixed on the opposite sides of the pin by means of the longitudinal strips 7 and 8 which are welded by electron bombardment as shown in FIG. 1. Due to the notches formed by its six equidistant shoulders, the pin has a scaly structure 14 which can be seen in FIG. 3, (which is at rightangles to FIG. 2) and ends in a leading portion which forms a point 15 designed to allow the pin to be easily pushed into the medular duct of the femur. This scaly structure could alternatively be provided up the entire height of the pin.

Figure 3:
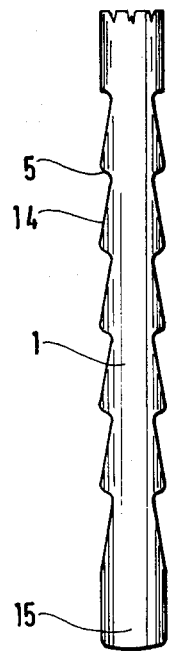
FIG. 3 is a partial elevation at 90° to that in FIG. 2.

The scaly structure can be seen in FIG. 3. The scales 14 form a constant angle of about 20° with the general plane of symmetry of the pin. Due to its circular profile, the central groove 3 has relatively wide zones 16 just above the shoulders and narrower zones 17 just below the wide zones and delimited by the oblique edges of the scales.

Once the lattice of titanium or titanium alloy wire is welded along the entire length of the pin, the assembly is coated with a long-lasting protective coating of titanium oxide. The simplest means of forming this coating is to proceed by anodic oxidation at 20 to 200 volts, preferably in a phosphoric acid bath in a normal solution to which boric acid may be added, the process being continued until a surface layer of anatase of 3000 to 3500 angströms is formed. However, an oxidizing gas can be used for gradual oxidation. When the pin used is made of the titanium alloy commercially known as "TA 6V" and which contains 6% aluminium and 4% vanadium, it is advantageous to coat it with anatase whose coefficient of expansion is very close to that of the "TA 6V" alloy, since that of rutile is not so close thereto.

Although the titanium or titanium alloy pin which has just been described with reference to the figures appears to be the best embodiment, it will be understood that various modifications can be made thereto without going beyond the scope of the invention, it being possible to replace some of its components by others which would perform an identical or analogous technical function. In particular, the shoulders can be more or less numerous and they need not necessarily be spaced apart regularly. The shape of the upper portion of the pin which connects it to the spherical head can be different.

The invention applies most particularly to a femoral pin for a hip prosthesis, but it extends generally to cement-free fixing of prostheses in long bones such as the femur, the tibia, the fibula or the humerus, in particular for prostheses of the knee or shoulder.

I claim:

1. A pin for cement-free fixing in a long bone to form a prosthesis of a joint or for bone repair, said pin being surrounded by a lattice of titanium wire with a mesh size of a least 0.3 mm, adapted to promote substantial even growth of bone tissue therethrough, having a substantially rectangular cross-section and wherein at least two of its opposite surfaces each includes a central longitudinal groove, and said pin at least two opposite surfaces being provided with successive transverse notches perpendicular to the general axis of the pin to form with said longitudinal groove a scaly structure on said two opposite surfaces.

2. A pin according to claim 1, wherein the transverse notches are evenly spaced out and are at a constant distance from the plane of symmetry of the pin between said opposite surfaces.

3. A pin according to claim 2, wherein the plane zones which separate the shoulders form an angle of about 20° with the plane of symmetry of the pin between its opposite surfaces.

4. A pin according to claim 1, wherein the pin is surrounded by two or three superposed lattices.

5. A pin according to claim 1 or 4, wherein the lattice or lattices of titanium wire are fixed to the pin by means of thin longitudinal strips of titanium or titanium alloy disposed on the outside of the metal lattice or lattices and welded to the pin by electron bombardment.

6. A pin according to claim 1, wherein the pin itself and the lattice are coated with a coating which protects them against long-term oxidation of the titanium.

7. A pin according to claim 6, wherein the protective coating against oxidation of the titanium is produced by anodic oxidation.

8. A pin according to claim 7, wherein the anodic oxidation is performed in a phosphoric acid bath.

9. A pin according to claim 7, wherein the protective coating is an anatase layer of 3000 to 3500 angstroms.

10. A pin according to claim 5, wherein the pin and the lattice are of a titanium alloy containing 6% aluminum and 4% vanadium, and the protective coating is a coating of anatase.

* * * * *